United States Patent [19]

Beyer et al.

[11] 4,025,620

[45] May 24, 1977

[54] TREATMENT OF CANINE OTITIS AND COMPOSITION THEREFOR

[75] Inventors: Detlef Beyer, Fredensborg; Anton Pedersen Linnet, Ballerup; Gerhard Thomsen, Farum, all of Denmark

[73] Assignee: Leo Pharmaceutical Products Ltd. A/S, Ballerup, Denmark

[22] Filed: Oct. 22, 1975

[21] Appl. No.: 625,626

[52] U.S. Cl. .............................. 424/115; 424/181; 424/239; 424/240

[51] Int. Cl.$^2$ ................ A61K 35/70; A61K 31/71; A61K 31/56

[58] Field of Search .......... 424/240, 239, 116, 115, 424/181

[56] References Cited

UNITED STATES PATENTS 3,821,375  6/1974  Alper ................................. 424/355

OTHER PUBLICATIONS

Winklmair–Chem. Abst., vol. 82, (1975), p. 93344w.
Merck Index–Eighth Edit., (1968), pp. 356, 477 & 478.

*Primary Examiner*—Sam Rosen
*Attorney, Agent, or Firm*—Lawrence Rosen; E. Janet Berry

[57] ABSTRACT

A liquid veterinary composition for treating canine otitis externa containing diethanolamine fusidate and an anti-fungal antibiotic such as nystatin. The composition additionally contains a broad spectrum antibiotic such as neomycin B sulphate, an anti-inflammatory agent such as prednisolone, and a vegetable oil as the suspending medium. The method of combating canine otitis externa by instilling said liquid composition in the dog's ear canal is also described and claimed.

5 Claims, No Drawings

TREATMENT OF CANINE OTITIS AND COMPOSITION THEREFOR

The present invention relates to a liquid composition, useful in the form of ear drops, for treating canine otitis externa and to the method of treating dogs to cure this disease. More particularly, the invention pertains to a liquid composition containing as essential ingredients diethanolamine fusidate and a veterinary-suitable fungicide. Additional components include a broad spectrum antibiotic and an anti-inflammatory agent. These active ingredients are suspended in a bland oil such as a vegetable oil.

Otitis externa is known to be one of the most common diseases in dogs. Although there have been a considerable number of publications dealing with this disease, some disagreement exists as to its etiology. Most investigators agree however that there is greater susceptibility to otitis externa in long-haired, pendulous-eared breeds of dogs rather than in dogs or other animals with erect ears, the latter type of ear being better ventilated. It has also been recognized that a very great proportion of ears with clinical signs of otitis externa are found with bacteria or yeasts; and whether or not these organisms are the causal agents, their elimination is usually followed by full or partial recovery.

Certain antibiotic preparations previously have been proposed for the treatment of otitis externa in the dog. One such commercial product is a neutral ointment containing sodium fusidate and sold under the tradename Funcidin Ointment. Panolog Ointment Veterinary and Toptic Ointment are other commercial products used for this purpose. Panolog Ointment Veterinary contains nystatin, neomycin sulphate, thiostrepton, and triamcinolone acetonide. Toptic Ointment contains cephalonium, polymyxin B sulphate, iodochlorhydroxyquin, piperocaine hydrochloride, and flumethasone. However, it was found that ointments are not always effective for treating canine otitis externa; probably because ointments, such as those described above, are non-melting and tend to stick in the outer portion of the ear or to remain in the upper portion of the auditory canal and therefore do not reach the infection site which may be somewhat deeper in the canal.

In accordance with the present invention a novel composition has been discovered which is highly effective against canine otitis externa. The composition of the invention is in liquid form and therefore can be employed as ear drops which avoids certain limitations encountered when using ointments. Ear drops have the further advantage of being easier to employ by non-professional treaters. Active ingredients in the composition include diethanolamine fusidate, a veterinary-acceptable fungicide, a broad spectrum antibiotic, and a veterinary-acceptable anti-inflammatory agent. These active ingredients are suspended in a bland oil which preferably is a vegetable oil.

Fusidic acid is a known compound, formerly designated Antibiotic ZN-6, which according to previous publications can be obtained by growing the fungus Fusidium coccineum Fuck (K. Tubaki) in an adequate fermentation medium. The compound has the elementary formula $C_{31}H_{48}O_6$ as described in U.S. Pat. Nos. 3,205,135 and 3,287,218. The sodium salt of fusidic acid, i.e., sodium fusidate, has been widely used in human pharmaceutical products such as those sold under the tradenames Fuciding H Ointment, Fucidin Gel, Fucidin H Gel, and Fucidin Caviject. However, for the present purposes the use of the diethanolamine salt of fusidic acid has been found to be very important, since the resulting liquid composition has greater stability, as evidenced by a longer shelf life, and discoloration problems are minimized. Diethanolamine fusidate is a narrow spectrum antibiotic which mainly combats staphylococci as described in U.S. Pat. No. 3,205,135.

The compositions of this invention must also contain an anti-fungal antibiotic. Although the use of nystatin (mycostatin), which is described in U.S. Pat. No. 2,797,183, is the preferred anti-fungal agent, other anti-fungals that may be employed are monosulfiram, tolnaftate, variotin, and miconazole.

The preferred broad spectrum antibiotic is neomycin B sulphate (framycetin sulphate) which has the elementary formula $C_{23}H_{46}N_6O_{13}$ as described on page 723 of the Merck Index, Eighth Edition. Although other members of the neomycin group as well as polymyxin and chloramphenicol may be utilized as the broad spectrum antibiotic ingredient in place of the neomycin B sulphate, the resulting compositions did not have the same high level of activity against canine otitis externa.

The anti-inflammatory agent is preferably a corticosteroid such as prednisolone, prednisone, triamcinolone acetonide, cortisone, hydrocortisone, flumethasone, dexamethasone, and the like. The especially preferred anti-inflammatory agent for the purposes of this invention is prednisolone.

The aforedescribed active ingredients are suspended in a bland oil. Vegetable oils such as sesame oil, cottonseed oil, cocoanut oil, soy bean oil, and peanut oil are preferred for the present purposes. In addition to acting as the suspension medium the oil has the further advantage of softening and dissolving ceruminous material.

The amounts of ingredients used in formulating the composition of this invention may range from about 2.5 to 10 mg non-toxic fusidic acid salt, 2.5 to 10 mg of the broad spectrum antibiotic such as neomycin B sulphate, 50,000 to 200,000 I.U. (international units, often referred to as "units of the anti-fungal antibiotic such as nystatin, and 1 to 20 mg of the anti-inflammatory agent based on each gram of the composition. It will be understood that the balance of the composition will be made up of the suspending oil, which will always be used in amounts that are at least sufficient to suspend all of the active ingredients and to yield a liquid composition. An especially preferred composition contains the following ingredients per gram:

| | |
|---|---|
| Diethanolamine fusidate | 5 mg |
| Neomycin B sulphate | 5 mg |
| Nystatin | 100,000 I.U. |
| Prednisolone | 2.5 mg |
| Sesame oil | up to 1.0 gm |

In combating canine otitis externa the composition of this invention is instilled in the auditory canal of the dog's ear. In general, 2 to 20 drops, preferably 5 to 10 drops, of the liquid composition should be instilled in the auditory canal usually twice daily. The extent of the topical treatment will, of course, depend upon each individual case. It has also been found advantageous in some instances to gently massage the auditory canal after instilling the drops to insure maximum penetration of the liquid composition.

The compositions of this invention may also contain other ingredients which may contribute to increasing the utility thereof for combating canine otitis externa. Such additional ingredients may encompass agents which will assist in destroying the bacterial pathogens, the gram negative and gram positive organisms, or the fungi associated with otitis externa. It is also possible to include other anti-inflammatory agents and the like which will be efficacious in treating the dog's ear canal or which will assist in the ensuring that the ear drops will readily penetrate the ear canal. Examples of the additional ingredients that may be employed are anaesthetics, parasiticides such as monosulfiram, and the like as well as mixtures thereof. Minor amounts of fat emulsifiers may also be employed when the ears contain large deposits of ceruminous material.

The invention will be more fully understood by reference to the following illustrative example.

EXAMPLE

A series of clinical trials were carried out with the following composition, each gram containing:

| | |
|---|---|
| Diethanolamine fusidate | 5 mg |
| Neomycin B sulphate | 5 mg |
| Nystatin | 100,000 I.U. |
| Prednisolone | 2.5 mg |
| Sesame oil | up to 1.0 gm |

The clinical trials were based on a random selection of suitable cases. Excluded cases were those caused by foreign bodies or parasites, those requiring systemic treatment, and those known to have had previous treatment within 28 days of the examination. Otherwise there was no selection made for type, duration, or severity.

In the trial group of 136 dogs, 99 had bilateral otitis; in 65 of these the microbiological findings in the two ears were identical, while in 34 dogs they were different. It was therefore more relevant for most purposes to count the number of affected ears than the number of dogs being treated. The breeds of dog represented in the clinical testing are listed in Table I below. For practical reasons all types of Spaniel (Cocker, Springer, etc.) were put together in one group, and the same applies to Poodles, Retrievers, etc.

TABLE I-continued

| Breed | No. |
|---|---|
| Dachshund | 6 |
| Newfoundland | 7 |
| Poodle (comb.) | 31 |
| Retriever (comb.) | 24 |
| Spaniel (comb.) | 22 |
| Wachtelhund | 2 |
| Setter (comb.) | 3 |
| Other breeds | 9 |
| Mongrel | 8 |
| Total | 136 |

At the initial clinical examination all relevant details of each case were recorded; a swab was taken for bacteriological examination and a thorough, mechanical cleaning of the affected ear(s) carried out. Correct application of the preparation was demonstrated and the owner instructed to instill eight to ten drops into the ear canal twice daily for two weeks.

The animals were subjected to a second clinical examination one week after the discontinuation of the treatment (i.e., three weeks after the initial examination). At a third and final examination a further seven days later a second swab was taken for bacteriological examination, and at each of the control examinations details of the progress of the patient were recorded.

Microbiology determinations were carried out by plate inoculation made from the swabs on:
a. 5% calf blood agar
b. 5% horse serum agar with 1% glucose
c. Sabouraud's glucose agar (4% glucose).

The swabs were then placed in nutrient broth and plates and broth incubated at 37° C. for approximately 24 hours. In case of a negative outcome of the primary cultivation on blood and serum agar a second cultivation was made, this time from the nutrient broth. In no such cases did growth of bacteria of pathogenic importance occur on these secondary plates.

The bacteriological diagnosis was based on the cultural features and biochemical reactions of the organisms as well as on their morphology and staining reactions. Haemolytic streptococci were classified after Lancefield.

The Sabouraud agar plates were examined after 2–4 days of incubation at 37° C., and the incubation thereafter continued; a final examination was carried out ten days after inoculation.

TABLE II

| Result of bacteriolog. examination prior to start of treatment | No. of ears treated | Compl. cured | | Consid. Improvement | | Slight improvement | | No. effect | |
|---|---|---|---|---|---|---|---|---|---|
| | | No. | percentage | No. | percentage | No. | percentage | No. | percentage |
| No organisms demonstrated | 50 | 36 | 72.0 | 8 | 16.0 | 2 | 4.0 | 4 | 8.0 |
| Growth of yeasts only | 55 | 41 | 74.5 | 7 | 12.7 | | | 7 | 12.7 |
| Growth of yeast and bact. | 67 | 55 | 82.1 | 9 | 13.4 | | | 3 | 4.5 |
| Growth of bact. only | 63 | 51 | 81.0 | 8 | 12.7 | | | 4 | 6.3 |
| Totals | 235 | 183 | 77.9 | 32 | 13.6 | 2 | 0.9 | 18 | 7.7 |

TABLE I

| Breed | No. |
|---|---|
| Alsatian | 12 |
| Bedlington Terrier | 2 |
| Boxer | 3 |
| Collie | 3 |
| Contin. Pointer | 4 |

TABLE III

| Microorganism | No. and percentage of ears found pos. at initial bact. examination | | No. and percentage of ears found pos. at final bact. examination | |
|---|---|---|---|---|
| | No. | percentage | No. | percentage |
| Yeast (Pityrosp.) | 123 | 52.3 | 21 | 8.9 |

TABLE III-continued

| Microorganism | No. and percentage of ears found pos. at initial bact. examination | | No. and percentage of ears found pos. at final bact. examination | |
| --- | --- | --- | --- | --- |
| | No. | percentage | No. | percentage |
| Staphylococci | 121 | 51.5 | 10 | 4.3 |
| Coliform. | 5 | 2.1 | 2 | 0.9 |
| Corynef. rods | 5 | 2.1 | 0 | 0 |
| Micrococci | 8 | 3.4 | 0 | 0 |
| Streptococci | 1 | 0.4 | 0 | 0 |
| Pseudomonas | 14 | 6.0 | 8 | 3.4 |
| Proteus | 8 | 3.4 | 2 | 0.9 |

A summary of the clinical results of the trials is set forth in Table II. As will be seen from the data, approximately 91% of all cases treated responded satisfactorily. Although the data collected during the testing indicated a higher rate of recovery for animals with no history of earlier treatment than for animals known to have been treated previously for otitis externa, the difference between the two groups was not statistically significant.

Table III presents the results of the initial and the final bacteriological examinations. This table shows the number of strains isolated on the primary plates at the initial and final examinations. The data in the Table reveals the excellent anti-bacterial and antimycotic effect of compositions containing both diethanolamine fusidate and nystatin.

While particular embodiments of this invention are shown above, it will be understood that the invention is obviously subject to variations and modifications without departing from its broader aspects. Thus, the liquid compositions of this invention may be employed for the treatment of otitis externa in a variety of animals which includes cats as well as dogs.

What is claimed is:

1. A liquid composition for the treatment of canine otitis externa which comprises 2.5 to 10 mg. of diethanolamine fusidate, 50,000 to 200,000 I.U. of nystatin, 2.5 to 10 mg. neomycin B sulphate, 1 to 20 mg. of prednisolone, and a sufficient amount of a vegetable oil such that the resulting admixture is in liquid form, said amounts being based on one gram of the liquid composition.

2. The liquid composition of claim 1 wherein said vegetable oil is sesame oil.

3. A method of combating canine otitis externa which comprises instilling drops of a liquid composition to the auditory canal of dogs, said liquid composition comprising 2.5 to 10 mg of diethanolamine fusidate, 50,000 to 200,000 I.U. of nystatin, 2.5 to 10 mg of neomycin B sulphate, 1 to 20 mg of prednisolone based on one gram of the liquid composition, and a vegetable oil.

4. The method of claim 3 wherein about 5 to 10 drops of the liquid ear drop composition is instilled into the dog's ear canal twice daily.

5. The method of claim 3 wherein said vegetable oil is sesame oil.

* * * * *